(12) United States Patent
Domb et al.

(10) Patent No.: US 6,442,423 B1
(45) Date of Patent: Aug. 27, 2002

(54) DEVICE FOR IONTOPHORETIC ADMINISTRATION OF DRUGS

(75) Inventors: Abraham Domb, Efrat; Joseph Frucht-Perry, Mevasseret Zion; Mervyn Shapiro, Jerusalem, all of (IL)

(73) Assignees: Hadasit Medical Research Services & Development Limited; Yissum Research Development Company of the Hebrew University of Jerusalem, both of Jerusalem (IL)

( * ) Notice: Subject to any disclaimer, the term of this patent is extended or adjusted under 35 U.S.C. 154(b) by 0 days.

(21) Appl. No.: 09/622,097

(22) PCT Filed: Feb. 5, 1999

(86) PCT No.: PCT/IL99/00077

§ 371 (c)(1),
(2), (4) Date: Sep. 25, 2000

(87) PCT Pub. No.: WO99/40967

PCT Pub. Date: Aug. 19, 1999

(30) Foreign Application Priority Data

Feb. 13, 1998 (IL) .................................................. 123290

(51) Int. Cl.⁷ ............................ B64D 10/00; B64G 6/00

(52) U.S. Cl. ........................... 604/20; 604/294; 604/501

(58) Field of Search ........................... 604/294, 20, 501

(56) References Cited

U.S. PATENT DOCUMENTS

| 5,676,648 A | 10/1997 | Henley | 604/20 |
| 6,101,411 A * | 8/2000 | Newsome | 604/20 |
| 6,319,240 B1 * | 11/2001 | Beck | 604/501 |

FOREIGN PATENT DOCUMENTS

| FR | 2 582 946 | 12/1986 |
| WO | WO 92/04937 | 4/1992 |
| WO | WO 92/04938 | 4/1992 |
| WO | WO 96/16693 | 6/1996 |

* cited by examiner

*Primary Examiner*—William Wayner
(74) *Attorney, Agent, or Firm*—Oliff & Berridge, PLC

(57) ABSTRACT

The present invention concerns a device (10) for administration of charged drugs to the eye comprising an applicator with a receiving portion for holding a hydrogel carrier loaded with the drug. The device also comprises an electric current generating element (15, 13, 14) for generating currents not exceeding 1000 $\mu$Amp coupled to a timing element (11) which ensures that currents do not last more than 120 secs.

12 Claims, 2 Drawing Sheets

DEVICE FOR IONTOPHORETIC ADMINISTRATION OF DRUGS

FIELD OF THE INVENTION

The present invention concerns a device for iontophoretic administration of drugs and more particularly to administration of drugs to the eye.

BACKGROUND OF THE INVENTION

The introduction of various drugs to the cornea of the eye, for example, administration of antibiotics for the treatment of microbial keratitus, is a complicated procedure. Presently, the routine treatment of microbial keratitus (MK) includes topical administration of highly concentrated antibiotics every 30 to 60 minutes day and night for several days. It should be noted that the bioavailability of a drug when administered in eye drops is very low (less than 1% of the administered dose) due to continuous rinsing of the drug by the tears.

An alternative method of administration of drugs is, by subconjunctival injections of antibiotics several times a day into the eye. The injections require a physician, are very painful and may cause severe complications such as perforation of the globe and scarring of the conjunctiva. Systematic administration of antibiotics is not effective in a vascular cornea.

Thus, there has been a constant search for development of alternative delivery techniques for overcoming the existing problems of administration of drugs to the eye. Some encouraging studies indicate efficacy of use of contact lenses soaked with highly concentrated antibiotics. However, these lenses may not be tolerable by patients with MK who commonly have inflamed and swollen conjunctiva and eye lids. There also have been some trials with liposomes incorporated with medicaments and use of laser, but these trials did not gain significant clinical acceptance.

Iontophoreesis (INT) is a noninvasive method which allows penetration of high concentrations of ionized molecules, such as drugs, into the tissue with the help of an electric current. In the past this method was utilized for anesthesia, for myringectomy, for diagnostic sweat testing in patients with cystic fibrosis and for administration of vidarabine in cases of herpes simplex. The drugs administered were steroids, antibiotics, peptides and analgesics. In ophthalmology, iontophoresis had been experimentally used in several animal studies to evaluate its efficacy in concentrating the drugs into the cornea or the eye. Barza[1] showed that transscleral INT using solutions may induce bactericidal concentrations of gentamicin (for several hours) in the vitreous of the monkey eye. Furthermore, repeated Electro Retino Graphia (ERG) tests did not show damage to the retina. Similar studies in the rabbit eyes presented high concentrations of gentamicin, cefazoline and ticarcillin in the vitreous[2]. Iontophoresis was also efficient for treatment of microbial endophthalmitis in the rabbit eye. It has been reported[3] that INT of tobramycin was more effective than topical administration of tobramycin for experimentally induced keratitus in the rabbit eye. INT of gentamicin via the cornea in aphakic rabbit eye revealed high levels of gentamicin in the vitreous. Finally, INT increased the penetration of ketaconazole (an antifungal drug) into the animals' anterior chamber[4].

The major limitations of INT in all prior art reports and trials were in the use of drug solutions which required complicated design of instruments needed in order to keep the fluid drug solution in contact with the desired tissue during the process of the iontophoresis. Handling of fluids to ensure their contact with a desired tissue is tricky, since the fluids leak, and form bubbles that reduce the efficacy of ionthophoretic process.

Another approach to iontophoretic administration of drugs to the eye was described by Grossman, who reported that marked concentrations of gentamicin can be transferred into the rabbit comes by INT when the drug gentamicin was incorporated in soft agar gel (instead of in a liquid solution)[5,6]. However, the use of agar has major limitations as follows: agar is a biologic material, so that each batch preparation of the agar results in slightly different products causing problems in the reproducibility of the drug administration; the shelf life of agar is very limited, it has to be kept in a refrigerated and moist environment rendering it impractical for prolonged storage; agar is fragile and requires expertise to be placed directly in contact with the ocular surface without breaking; and finally some of the agar material will always stay on the ocular surface, causing irritation, eye redness and inflammation.

It would have been highly desirable to provide a device for iontophoretic administration of drugs to the eye which would be easy to operate, safe and would minimize damage to the eye.

SUMMARY OF THE INVENTION

The present invention concerns a device for iontophoretic administration of charged drugs to the eye comprising:

an applicator formed with a receiving portion adapted for holding a replaceable hydrogel carrier loaded with said drug and allowing contact of the carrier with a surface of the eye;

an electric current generating element, for generating currents not higher than about 1000 $\mu$Amp, being electrically coupled to the said receiving portion such that the current once generated passes through the hydrogel carrier in a direction essentially normal to said surface;

a timing element for activating the electrical current generating element for pre-set periods of time not exceeding 120 seconds; and a switch for activating said timing device.

The device of the present invention is suitable for safe administration of iontophoretic drugs into the eye which do not exceed pre-set periods, and do not exceed maximum level of electric current. The device of the invention enables safe reproducible and repeated administration of drugs to the eye.

The term "charged drugs" refers to drugs which may be a priori charged, to the drugs which become charged in a solution with which the hydrogel carrier is loaded, as well as to drugs which are initially not charged, but become charged in the presence of an electrical current.

Examples of commonly used charged drugs include antibiotics such as: gentamicin, tobramycin, vancomycin; antifungal drugs including: miconazole, ketoconazole; anti-inflammatory agents such as: ibuprofen and its derivatives; timolol; steroids; anti glaucoma agents such as: pilocarpine; anticancer agents such as mitomicin C, methotrexate and 5-FU which are delivered to treat cancer of the eye or cornea; local anesthetics which are delivered to the eye and to the conjuctiva to anesthetize the eye before a treatment or reduce pain, such as lidocaine, bupivacaine and benoxinate.

The term "eye" refers to the external regions of the eyes and includes the cornea, conjunctiva, sclera, eye lids and lid margins.

The device comprises an applicator having a receiving portion which can hold a replaceable hydrogel carrier, that is loaded with the drug. The applicator is in the form which allows contact of the carrier and the surface of the eye. The applicator may be held by a specific external fixing device, for example, during an operation to ensure its position, but preferably, for ease of operation it should be hand held. The applicator may form a separate component of the device of the invention, or alternatively, the whole device of the invention may be in the form of a single instrument wherein the applicator is an integral part thereof.

The applicator has a receiving portion, for example in the form of an indention, or in the shape of a half-circle ring for holding a replaceable hydrogel carrier which is loaded with the drug. Preferably the indention is conical or cylindrical to accommodate a hydrogel carrier having a corresponding shape. Typically, the applicator or the whole device (when applicator is integral with the device) is in the shape of an elongated rod where the receiving portion is at the end of the rod.

The device includes an electrical current generating element which can be battery operated or connected to an external AC power source, for the generation of currents which are not higher than about 1000 $\mu$Amp. The electrical current generating element is positioned so that it is electrically coupled to said receiving portion. In operation, when a hydrogel carrier is fitted within the receiving portion, the electrical current generating element, generate currents that pass through the hydrogel in a direction substantially normal to the surface of the eye, thus causing the migration of charged drugs from the hydrogel carrier to the eye. both due to electrical field as well as due to diffusion. Preferably, the device should also comprise an electric control element which can control the level of the current passed into the gel to a pre-set current. For example, the physician may decide to apply a current of a specific level by properly adjusting the control element.

The device should also include a timing device for activating the electrical current generating element for pre-set periods of time not exceeding 120 seconds. Thus in operation, the physician or the patient itself, may choose a preset period of time, and a pre-set level of electric current (by adjusting the electric control element), and by mere activation of the switch, produce an electrical current of a fixed duration and level.

Where the device of the invention is battery operated, and the device is in the shape of an instrument having an applicator integral therewith, the device should also contain a recess for holding the battery.

The ground element of the device, may be in the form of a separate wire extending externally from the applicator, which can be in touch with any part of the patient's body, preferably on his face, to serve as ground.

By another aspect, the present invention concerns a system for iontophoretic administration of drugs to the eyes, comprising a device as described above, and a drug loaded hydrogel carrier which carrier has a shape and size so as to be accommodated by the receiving portion of said device. For example, where the receiving portion is conical or cylindrical, the carrier is in the form of conic or cylindric disc, respectively, having a size which precisely matches that of the receiving portion. Where the receiving portion is in the shape of a half ring the carrier is in the shape of a round disc. Preferably, the calibration size of the carrier should be in the size range of 0.2 mm (for administration to small regions of the eye) to about 20 mm, (for example, for administration to the whole region of the eye in larger animals such as cattle).

It is also possible to produce a system for iontophoretic administration of the eye, wherein the receiving portion is adjustable, so it can receive various hydrogel carriers of various sizes, so that a single applicator is suitable for many sizes of hydrogel carriers, for example the receiving portion may include a ring with an adjustable diameter which holds the carrier.

By a third aspect, the invention concerns a hydrogel carrier for use in the above system, comprising a hydrogel material having at least 50% w/w water content; the hydrogel carrier being impregnated with the charged drug. Typically, the hydrogel carrier should be in the shape of a conical or cylindrical disc.

The hydrogel material that is suitable for this application should contain at least 50% w/w of water to allow free transport of the drug through the gel; it should be compatible with the eye; be inert to the loaded drug and safe at storage and during application should not release any unwanted small irritating/toxic molecules; stable during the life of the application; it should be physically and chemically stable in order to maintain its shape and size and its chemical and physical integrity; and generally should be comfortable in contact with the eye.

The hydrogel material is typically uncharged but may contain anionic (carboxylates) or cationic (amino groups) residues to enhance drug release upon application of a current pulse. The hydrogel may contain other organic or inorganic ions and salt solutions. Hydrogel discs are prepared from various known hydrogel compositions including: acrylic based hydrophilic monomers, crosslinked, polysaccharides and polyols, and crosslinked polyethylene glycols. Various compositions of hydrogels are described in the literature[7].

The charged drugs are loaded into the hydrogel carrier either during the preparation of the gel (for example during the polymerization process) or by placing a pre-prepared carrier pellet in a drug solution so that the gel absorbs the solution.

The present invention further concerns a method for the administration of charged drugs to the eye comprising:

(i) contacting a substance of the eye with a hydrogel carrier impregnated with said drug;

(ii) passing a current through said carrier at an intensity below about 1000 $\mu$Amp for a period not exceeding 120 seconds and in a direction normal to said surface, thereby causing the charged drug to migrate from said carrier to the eye.

Preferably the method should make use of the system of the invention. The method is suitable for medicinal and veterinary purposes.

In the following, the invention will be further described with reference to some non-limiting drawings and examples.

DETAILED DESCRIPTION OF THE INVENTION

Figure 1:
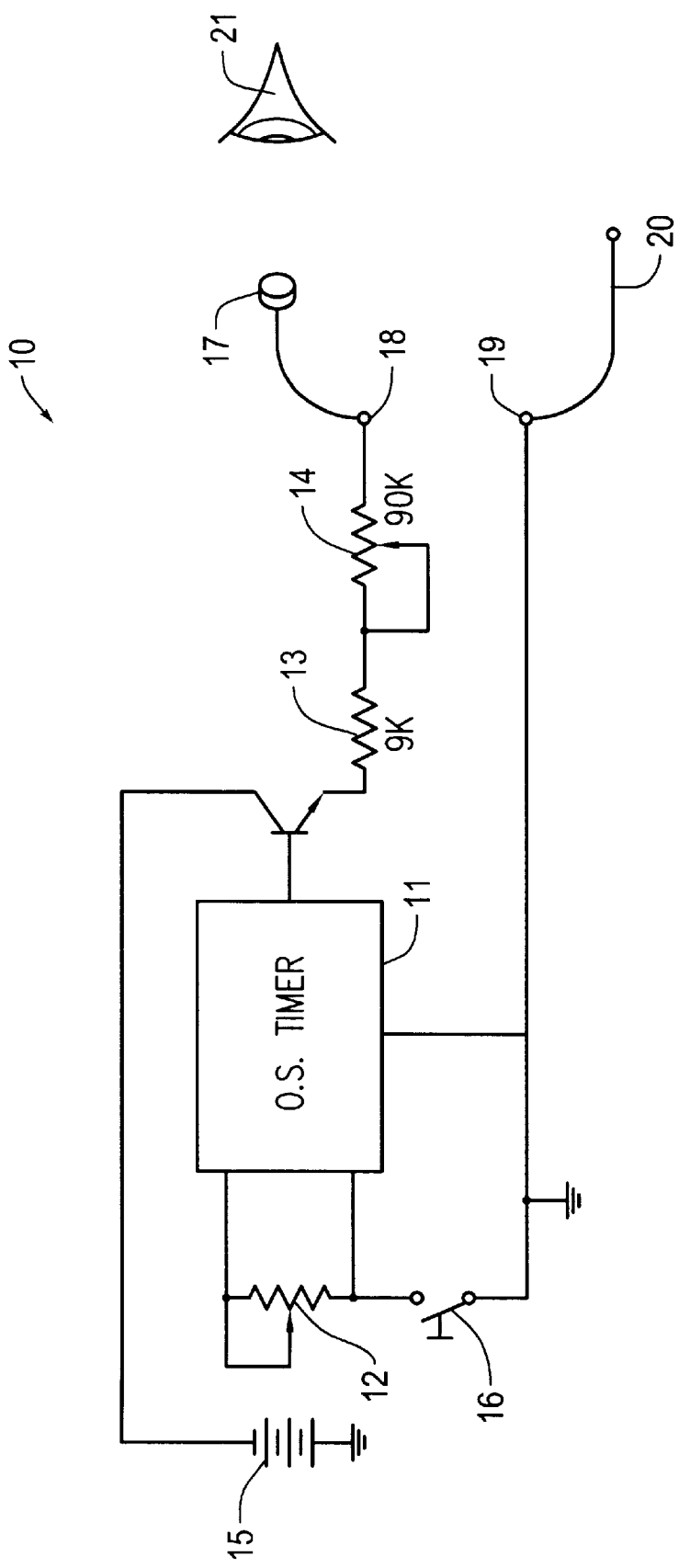
FIG. 1 shows a schematic representation of the electronic components of the device of the invention.

Reference is now made to FIG. 1 which schematically shows the main electronic component of the device of the invention 10. The device is composed of an O.S. timer 11 connected to adjustable component 12 for adjusting the time between 10 and 120 seconds.

The timer is electrically coupled to a resistor of 9 K 13 which is in-line coupled with an adjustable resistor of 90 K 14, which adjustable resistor can tune the current between 100 and 1,000 μAmpere.

The electronic components are powered by a power source 15, for example a battery, and is the electronic circuitry activated by switch 16.

The hydrogel disk 17 is connected to the cathode end of the electronic component 18 while the anode 19 has a wire 20 extending therefrom which is connectable to an external body surface other than the eye. In operation, the physician sets the desired current by adjustable resistor 14, sets the desired time by time tuning component 12, places disk 17 on eye 21, and then closes switch 16 to activate the system. Meanwhile wire 20 is placed on an external part of the patient's body, for example, his ear, cheek, etc.

Figure 2:
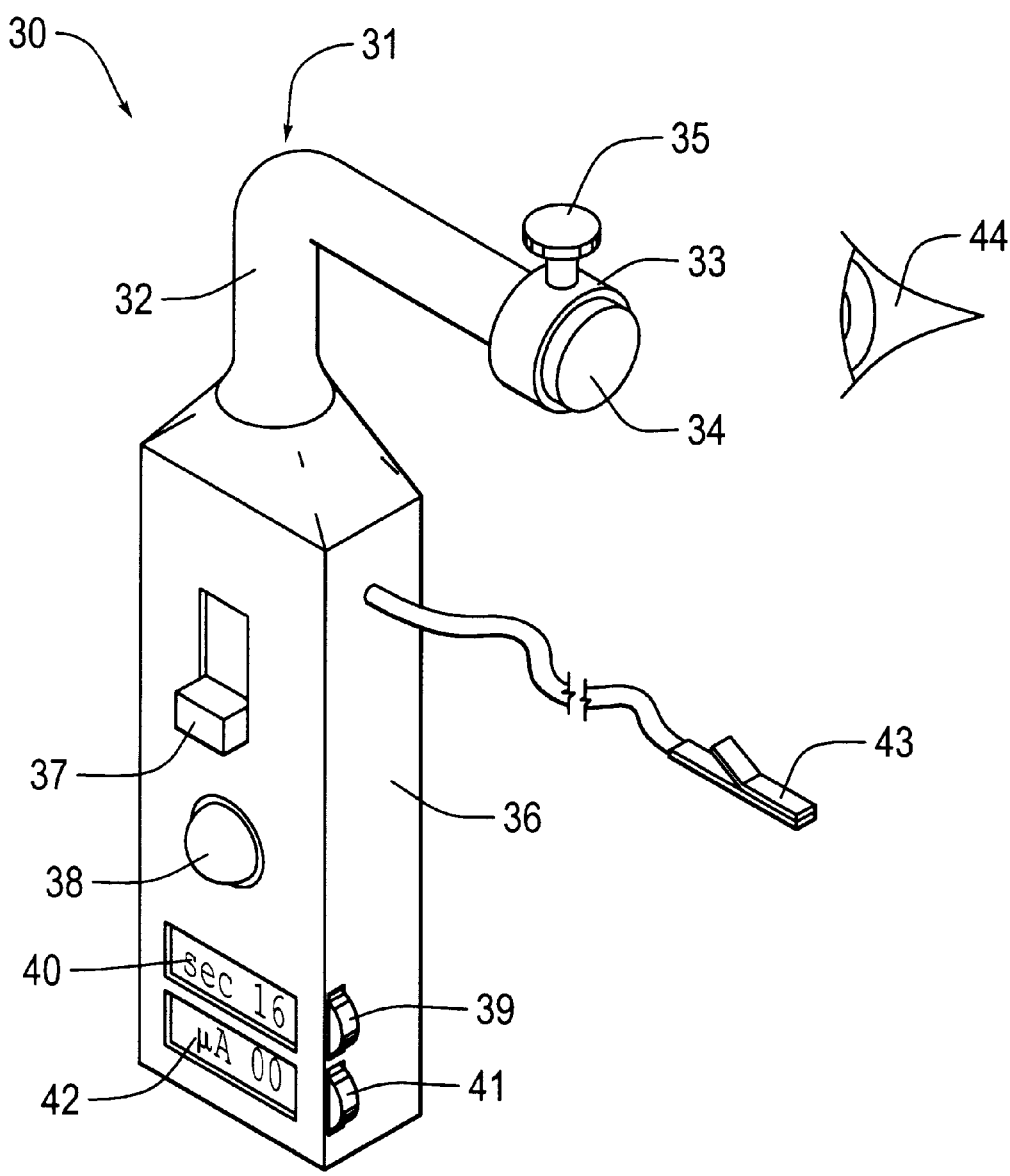
FIG. 2 shows a schematic representation of the device of the invention.

Reference is now made to FIG. 2, which shows a schematic representation of the device of the invention 30. The device has a receiving portion 31 composed of an L-shaped arm 32 extending from the body of the device, and an adjustable ring 33, which claps the hydrogel carrier 34. Ring 33 may accommodate hydrogel carrier discs of various dimensions, by adjusting, with screw 35, the diameter of the ring.

The container of the device 36, holds the electronic components shown schematically in FIG. 1. More specifically, it has an on/off switch 37, and a push button 38 (corresponding essentially to electronic component 16 in FIG. 1), which when touched gives pulses of a pre-set length and magnitude.

The device has a time control button 39 (corresponding essentially to electronic component 12) and a digital time display window 40, and a current control button 41 (corresponding to component 14 in the electronic circuitry) and a digital current display window 42.

The anode of the device is connected to wire 43.

In operation, hydrogel 34 is placed on eye 44, and wire 43 is placed on any external part of the patient, for example, the ear, cheek, in his mouth, etc.

I. PREPARATION OF POLYMERIC HYDROGELS

EXAMPLE 1

Preparation of Disposable Hydrogel Loaded With Gentamicin

The hydrogels were prepared by polymerization of solutions containing methylmethacrylate (MMA, 0–10%), heydroxyethylmethacrylate (HEMA, 3–50%), ethyleneglycol dimethacrylate (EGDMA, 0–5%), gentamicin (0–20%), water (20–95%) and a radical source (redox mixture, $Na_2S_2O_5$ and $Na_2S_2O_g$.) The solutions were cast between two flat glasses to form a film or into conic vials and polymerized at room temperature overnight. The polymerized gels were cut into the appropriate size to fit the end of a probe.

Gentamicin was loaded into the gel either during polymerization of the metomer or by absorption from a 10% aqueous solution of gentamicin. Other useful uncharged monomers which may be used are acrylamide and its derivatives, N,N-ethylenediacrylamide, glycerol methacrylate, and N-vinylpyrrolidone. Charged monomers are methacrylic and acrylic acid, aminoethylmethacrylates, vinylpyridines and vinylimmidazoles.

In a typical preparation, HEMA (2.0 ml), EGDMA (0.04 ml), gentamicin sulfate (100 mg), water (2.0 ml) and a redox mixture of 2% w/v $Na_2S_2O_g$ (0.05 ml) and 2% w/v $Na_2S_2O_g$ (0.05 ml) are mixed to form a uniform solution. The solution was purged with dry nitrogen and then cast in between two flat glasses separated with a gasket of 2 mm and left to polymerize overnight at room temperature. The solid membrane was cut into circular discs of 3 mm in diameter.

Alternatively, the same polymer composition was prepared but without the drug and cast into a solid membrane of 2 mm thick. The membrane was cut into discs and the discs were dehydrated by lyophilization. The dried discs were allowed to hydrate into a 10% w/v gentamicin sulfate solution for 24 hours at room temperature. The hydrated discs were blotted with a sterile tissue prior to use.

EXAMPLE 2

Preparation of Polysaccharide Gels a. Albumin cross linking oxidized Arabinogalactan (AG)

Albumin, a natural compatible protein containing amine groups, was reacted with increasing amounts of oxidized AG in order to obtain a cross-linked gel. The experiment was as follows: 1.0 gr. of egg-albumin (or bovine serum Albumin) was dissolved in 5.0 ml of 0.1 M $NaHCO_3$, the solution was incubated for 15 min. at 37° C. to obtain a clear-yellow solution which was reacted with a concentrated solution of oxidized AG (1.0 g in a 2 ml solution) for 24 hours at 37° C. to form an insoluble gel. Other proteins such as gelatin, chitosan, and collagen were also used instead of albumin.

b. Lysine cross linking with oxidized Arabinogalactan 1.0 g of di-aldehyde Arabinogalactan (35% degree of oxidation) was dissolved in 4.0 ml deionized water and 25 mg of lysine hydrochloride was added to the polymer solution and the pH was adjusted to 8.0 using 0.1M NaOH solution. Under these conditions cross linking is fast. At the alkaline pH of the water phase, reaction of lysine with di-aldehyde Arabinogalactan proceeds rapidly and the gel hardened. The obtained gel was washed with water several times to remove soluble matters and dried in vacuum (yield=~90% by weight).

Reduction of the Imine-bond obtained in the gel was done by incubating the gel in sodium borohydride solution (1.5 mol $NaBH_4$ for each 1 mol sugar units of polysaccharide) for 4 hours at room temperature followed by filtration and washing with water. The reduced gel was placed in ethanol at 4° C. overnight, isolated and dried in vacuum. Gels with increased cross linking were obtained by reacting the oxidized polysaccharide with increasing amounts of lysine up to about 20% by weight per polymer. Other diamine molecules such as ethylene diamine, hexamethylene diamine and polyethylene imine can be used instead of lysine.

The dry gel was loaded with gentamicin by immersing the gel in a 10% gentamicin sulfite solution for 24 hours.

EXAMPLE 3

Preparation of Polyurethane Gels

Polyurethane gel was prepared from Hypol PreMA G-60 (Hampshire Chem. Corp. Owensboro, Ky., USA) which is a reactive diisocyanate). The gel film was prepared by diluting the viscous Hypol in acetone (1 part in 2 parts) and then adding 2 parts of water. The solution was mixed well and the homogeneous solution was cast into a dye and allowed to solidify. The solution was solidified within 15 mins. and the polymerization was allowed to complete over night. The solid gel was placed in deionized water for 24 hours to extract impurities, cut into discs on 4×2 mm and then lyophilized. The clear and flexible dry discs were placed in a 10% by weight of gentamicin sulfate to absorb the solution and the hydrated gels were blotted with a paper tissue and weighed. The hydrated discs contained 92% of solution.

These discs are suitable for iontophoresis administration of gentamicin to the eye.

EXAMPLE 4

Preparation of Hydrogel Pellets Loaded With Drugs

Acrylic gel membranes prepared from cross-linked HEMA with 0.2–3% w/w of EGDMA or ethylenediacrylamide which absorb 85% of water. The membranes were freeze-dried to dryness following drug absorption/loading by immersing the polymer discs in 10% drug solutions in aqueous solutions (i.e. buffer solutions, mixtures of water with hydrophilic solvents such as alcohol, DMSO, DMF and THF) overnight. Loading of 5 to 50 mg drug/ml hydrated gel was obtained. The following drugs were incorporated into the acrylate gel: ibuprofen, fluoprofen, timolol, miconazole, pilocarpine, tobramycin, vancomycin, and peptides including LHRH and TRH.

II. BIOLOGICAL TESTS

The release of gentamicin from hydrogel probes (prepared in Example 1 into rabbits' eyes) using iontophoresis was determined by the following two experiments:

EXAMPLE 5

Release of Gentamicin Into The Rabbit Eye Using Hydrogel-Probe Iontophoresis

Thirty six healthy rabbits (age 2–3 months, weight 2000 grams) were used. The study conformed with the ARVO Resolution of the Use of Animals in Research. The animals were anesthetized with intramuscular injections of ketamin HCl 1 mg/kg (Park Davis, Morris Plains, N.J.) and xylazine 50 mg/kg (Mobay, Shawnee, Kans.). Iontophoresis was carried out as follows: the distal end of the hydrogel-probe placed in a device as shown in FIG. 2 (diameter of 3 mm and 2 mm thick) was gently applied to the cornea of the rabbit while the anode of the iontophoretic system is inserted into the other end of the device and the cathode is attached to the ear of the animal.

A single concentration of 10 mg/ml gentamicin in the hydrogel-probe (dd) was studied, using two time periods of iontophoresis: long periods (60 seconds) and short periods (10 seconds). Six groups of rabbits, 6 animals per group, were treated with one of the treatments described in the following Table 1.

TABLE 1

| Group Number | Treatment | Gentamicin concentration in dd (mg/ml) | Current (mAmp) |
|---|---|---|---|
| 1 | 60 sec. INT + drug | 10 | 0.5 |
| 2 | 10 sec. INT + drug | 10 | 0.5 |
| 3 | 20 drops hr | 0.3% drops | NA |
| 4 | 60 sec. no current | 10 | 0 |
| 5 | 10 sec. no current | 10 | 0 |
| 6 | 60 sec. INT no drug | 0 | 0.5 |

In group 3, one drop of topical gentamicin (14 mg/ml) was instilled into the eye every 5 minutes for 1 hour. In groups 4 and 5, mock iontophoresis was performed by placing a device containing 10 mg/ml of gentamicin on the cornea for 60 and 10 seconds without switching on the electric current. In group 6 iontophoresis was applied for 2 minutes with the dd containing NaCl 0.9% (instead of gentamicin).

Ten minutes after completion of the iontophoresis, or the control drug delivery technique in each animal, the surface of the eye was washed with 5 ml of NaCl 0.9%. The animals were sacrificed after 15 minutes by injecting an overdose of sodium pentobarbital. The entire cornea was excised with corneal scissors and rinsed again with 5 ml of NaCl 0.9%. The cornea was weighed, minced with a blade and placed into microcentrifuge tubes. To each tube, 0.5 ml 0.01 M phosphate buffered saline (pH 7.2) was added. The tubes were incubated for 18 hours in a water bath heated to 37° C., shaking at 100 oscillations/min. Thereafter the tubes were centrifuged for 10 min. at 2000 rpm. From each tube 125 microliter of the supernatant were assayed for gentamicin concentration using Abbot $TD_x$. The concentration of gentamicin in the cornea was calculated as described before[5]. Gentamicin concentrations are expressed in micrograms per gram of tissue or per milliliter of buffer. 3 way ANOVA test was used for statistical evaluation.

The results are shown in the following Table 2.

Results:

TABLE 2

Gentamicin concentration in the cornea after iontophoresis application
Gentamicin concentration in cornea (mcg/g)

| | Eye No. | | | | | | |
|---|---|---|---|---|---|---|---|
| Group No. | 1 | 2 | 3 | 4 | 5 | 6 | Average |
| 1 (0.5 mA/ 60 sec) | 32.0 | 24.6 | 53.3 | 30.7 | 28.0 | 30.0 | 33.1 ± 9.3 |
| 2 (0.5 mA/ 10 sec) | 6.27 | 6.53 | 4.92 | 6.70 | 7.05 | 7.52 | 6.5 ± 0.8 |
| 3 (eye drops) | 1.59 | 1.46 | 4.16 | 2.05 | 1.03 | 2.47 | 2.1 ± 1.0 |
| 4 (0.0 mA/ 60 sec) | 2.01 | 2.55 | 2.78 | 2.89 | 2.70 | 2.96 | 2.6 ± 0.3 |
| 5 (0.0 mA/ 10 sec) | 1.12 | 1.23 | 0.37 | 1.25 | 1.21 | 1.68 | 1.1 ± 0.4 |
| 6 (0.0 mA/60 sec/no drug), no irritation to the eye | | | | | | | 0.0 ± 0.0 |

Experiment 6

The purpose of this experiment was to determine the effect of the current applied and duration on the drug cornea concentration. In this experiment, 27 Albino rabbits were divided into 9 study groups as shown in Table 3. Each group of 3 rabbits (6 eyes) were treated with iontophoresis and the results are given in Table 4.

TABLE 3

Animal group design by: concentration of gentamicin in hydrogel probe (dd), duration and current of iontophoresis

| Group No. | Treatment | Gentamicin concentration in dd (mg/ml) | current (mAmp) |
|---|---|---|---|
| 1 | 60 sec. INT | 10 | 0.0 |
| 2 | 60 sec. INT | 10 | 0.1 |
| 3 | 60 sec. INT | 10 | 0.3 |
| 4 | 10 sec. INT | 10 | 0.6 |
| 5 | 10 sec. INT | 10 | 0.0 |
| 6 | 10 sec. INT | 10 | 0.1 |
| 7 | 10 sec. INT | 10 | 0.3 |
| 8 | 10 sec. INT | 10 | 0.6 |
| 9 | SC inj. | 0.3% w/v | NA |

Results

TABLE 4

Gentimicin concentration in the cornea after iontophoresis application - effect of time and current applied

| Group No. | Eye No. 1 | 2 | 3 | 4 | 5 | 6 | Average |
|---|---|---|---|---|---|---|---|
| 1 (0.0 mA/60 sec) | 2.5 | 1.3 | 3.3 | 2.4 | 0 | 6.7 | 2.71 ± 2.0 |
| 2 (0.1 mA/60 sec) | 4.2 | 4.5 | 11.0 | 1.4 | 1.6 | nd | 4.5 ± 3.5 |
| 3 (0.3 mA/60 sec) | 18.3 | 34.4 | 87.4 | 14.1 | 56.7 | nd | 42.2 ± 27.1 |
| 4 (0.6 mA/60 sec) | 144.3 | 56.6 | 32.6 | 95.8 | 75.2 | 127.0 | 88.6 ± 38.6 |
| 5 (0.0 mA/10 sec) | 0.0 | 0.0 | 0.0 | 2.4 | 0.0 | 0.0 | 0.0 |
| 6 (0.1 mA/10 sec) | 0.6 | 2.3 | 8.3 | 3.9 | 3.6 | 5.6 | 4.0 ± 2.4 |
| 7 (0.3 mA/10 sec) | 7.0 | 6.2 | 11.3 | 9.7 | 18.7 | 8.4 | 10.2 ± 4.1 |
| 8 (0.6 mA/10 sec) | 29.6 | 22.2 | 25.5 | 22.8 | 26.5 | 5.4 | 22.0 ± 7.8 |
| 9 (subconj. inj.) | 37.6 | 19.5 | 22.3 | 14.8 | 17.6 | 68.2 | 30 ± 18.6 |

As can be seen, an increase in the gentamicin concentration is found with increase duration and amplitude of the electric current Iontophoretic application using the hydrogel disc for 60 sec. at a 0.3 mAmp provided similar concentrations to the painful injection to the subconjunctiva (SC). Applying a current of 0.6 mAmp resulted in a 3 times increase in drug concentration as compared with SC injections and about 30 times over a non-current application (diffusion only). High gentamicin concentrations were found in the intraocular fluid for Groups 3 and 4.

EXAMPLE 7

Toxicity and Irritation Studies

HEMA based hydrogel discs with or without gentamicin were applied on the eye surface for up to 120 seconds and with an increasing current up to 1 mAmp. The eyes were isolated and evaluated histopathologically to determine any damage to the eye surface. No acute or long term damage to the eye or to the general health of the rabbits was found. The animals tolerated the devices and all tissues were normal and intact.

REFERENCES

1. Barza, M. et al., *Inve. Ophthalmol. Vis. Sci.*, 154:1033 (1987).
2. Barza, M. et al., *Ophthalmology*, 93:133 (1986).
3. Barza, M. et al., *Inves. Ophthalmol. Vis. Sci.*, 28:1033 (1987).
4. Grossman, R. E., et al., *Ophthalmology*, 93:133 (1986).
5. Grossman, R. E., et al., *Inves. Ophthalmol. Vis. Sci.*, 31:909 (1990).
6. Frucht Pery, J., et al., *Inves. Ophthalmol. Vis. Sci.* (Supp), 3914 (1993).
7. Dumitriu, S., *Polymeric Biomaterials*, (Editor) Marcel Dekker, NY, 3–85, (1993).

What is claimed is:

1. A device for iontophoretic administration of charged drugs to the eye comprising:
    an applicator formed with a receiving portion adapted for holding a replaceable hydrogel carrier loaded with said drug and allowing contact of the carrier with a surface of the eye;
    an electric current generating element, for generating currents not higher than about 1000 μAmp, being electrically coupled to the said receiving portion such that the current once generated passes through the hydrogel carrier in a direction essentially normal to said surface;
    a timing element for activating the electrical current generating element for pre-set periods of time not exceeding 120 seconds; and
    a switch for activating said timing device.

2. A device according to claim 1, wherein the applicator is hand held.

3. A device according to claim 2 in the form of a hand held instrument with said applicator being integrally formed therein.

4. A device according to claim 3, having the shape of an elongated member with the applicator formed at one end thereof.

5. A device according to claim 1, wherein the receiving portion is formed with an indention for receiving a hydrogel carrier pellet.

6. A device according to claim 5, wherein the indention is adapted to receive a cylindrical hydrogel pellet.

7. A device according to claim 1, wherein the receiving portion is formed as a section of a ring or as a ring having an adjustable dimension.

8. A device according to claim 3, wherein the electric element is battery operated and the instrument includes a receptacle for holding batteries.

9. A device according to claim 1, having a ground element as a wire externally from the applicator.

10. A device according to claim 1, comprising an electric current control component for adjusting the level of electric current produced by the electric current generating element, to pre-set levels.

11. A system for the iontophoretic administration of drugs to the eye comprising a device according to claim 1, and a drug-loaded hydrogel carrier of a shape and size such so it may be accommodated within the receiving portion of said device.

12. A method for the administration of charged drugs to the eye comprising:
    (i) contacting a substance of the eye with a hydrogel carrier impregnated with said drug;
    (ii) passing a current through said carrier at an intensity below about 1000 μAmp for a period not exceeding 120 seconds and in a direction normal to said surface, thereby causing the charged drug to migrate from said carrier to the eye.

\* \* \* \* \*